United States Patent [19]

D'Souza et al.

[11] 4,122,252
[45] Oct. 24, 1978

[54] PROCESS FOR THE PREPARATION OF ESTERS

[75] Inventors: Richard D'Souza; Pierre-Charles Wyss, both of Muttenz, Switzerland

[73] Assignee: Hoffmann-La Roche Inc., Nutley, N.J.

[21] Appl. No.: 855,857

[22] Filed: Nov. 30, 1977

[30] Foreign Application Priority Data

Dec. 2, 1976 [CH] Switzerland .................. 15185/76

[51] Int. Cl.² ........................................... C07H 17/00
[52] U.S. Cl. ...................................... 536/23; 424/180
[58] Field of Search ............................... 536/23, 29

[56] References Cited
PUBLICATIONS

Reese, C., et al., J. Chem. Soc. Perkin Trans. I (GB) No. 10 (1975).
Logue, M., Carbohydrate Research 40 C9–C11 (1975).

Primary Examiner—Johnnie R. Brown
Assistant Examiner—Blondel Hazel
Attorney, Agent, or Firm—Samuel L. Welt; Jon S. Saxe; George M. Gould

[57] ABSTRACT

The present invention relates to a process for the manufacture of esters. More particularly, the invention is concerned with a process for the manufacture of esters of 2,2'-anhydro-1β-D-arabinofuranosyl-5-fluorocytosine.

2 Claims, No Drawings

PROCESS FOR THE PREPARATION OF ESTERS

BACKGROUND OF THE INVENTION

Fromageot et al., in Tetrahedron 23, 2315 (1967) describe the reaction of ribonucleosides, such as cytidine, with trimethylorthoacetate to yield the corresponding 2',3'-O-methoxyethylidene derivative and then hydrolyzing with aqueous acid under mild conditions to produce a mixture of 2'- and 3'-O-acetates in a yield of 74%.

Logue in Carbohydrate Research 40, C9–C11 (1975) discloses the reaction of 2',3'-O-(methoxyethylidene)-uridine with trimethylchlorosilane in acetonitrile under reflux for 10 minutes to produce 3'-O-acetyl-2,2'-anhydro-1β-D-arabinofuranosyluracil hydrochloride in 72% yield.

U.S. Pat. No. 3,709,874 describes the preparation of 3'-O-acyl-2,2'-anhydro-1β-D-arabinofuranosyl-5-fluorocytosines by selective hydrolysis of the corresponding 3',5'-O-diacyl derivatives.

DESCRIPTION OF THE INVENTION

The esters obtained according to the process of the present invention have the following general formula

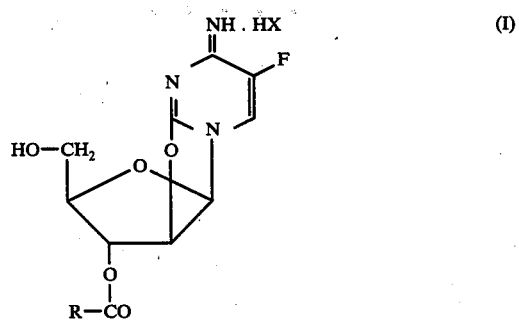

(I)

wherein R represents an alkyl group containing from 1 to 6 carbon atoms, especially the methyl group, and X represents halogen, especially chlorine or bromine.

According to the present invention, the esters of formula I hereinbefore are manufactured by reacting 5-fluorocytidine in the presence of an acid with an orthoester of the general formula $$R—C(OR^1)_3 \qquad (II)$$

wherein R has the significance given earlier and $R_1$ represents an alkyl group containing from 1 to 3 carbon atoms, and heating the mixed orthoester of the general formula

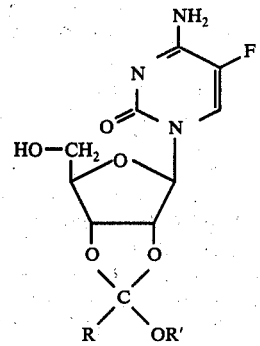

(III)

wherein R and $R^1$ have the significance given earlier, obtained as the reaction product in a solvent with a halogen compound which contains covalently bound, readily cleavable halogen, and, if desired, subjecting a thus-obtained compound of formula I in which X represents halogen to an anion-exchange to produce other physiologically acceptable acid addition salts.

The acid used in the reaction of 5-fluorocytidine with an orthoester of formula II is conveniently p-toluenesulphonic acid, although other acids (e.g. Lewis acids) can also be used. The amount of acid used is not especially critical; as a guideline there can be mentioned 0.1–1 mol or somewhat more of acid per mol of 5-fluorocytidine.

This acid-catalysed reaction can be carried out at room temperature. If desired, the reaction mixture can be cooled externally.

The orthoester of formula II is conveniently used in up to a 5-fold molar excess. Orthoacetic acid trimethyl ester ($R = R^1 =$ methyl) is the preferred orthoester, but triethyl orthoesters or tripropyl orthoesters of acetic acid, propionic acid, butyric acid and the like can also be used.

The foregoing acid-catalysed reaction yields a mixed orthoester of formula II such as, for example, 2',3'-O,O-(1-methoxyethylidene)-5-fluorocytidine ($R = R^1 =$ methyl). The mixed orthoesters of formula III are novel and it will be appreciated that they also form part of the present invention.

In order to convert a mixed orthoester of formula III into a desired ester of formula I, the mixed orthoester is heated with a halogen compound which contains covalently bound, readily cleavable halogen. Examples of such halogen compounds are trimethylchlorosilane, trimethylbromosilane and other tri(lower alkyl)halosilanes, triphenylchloromethane and other triarylhalomethane compounds. This heating is carried out in the presence of a solvent, conveniently a polar, hydroxyl-free solvent and preferably acetonitrile, the nitrile of another lower aliphatic carboxylic acid or a nitroalkane such as nitromethane. The solution of the reaction partners is advantageously heated to boiling under reflux.

The product is obtained in the form of an acid addition salt of formula I in which X represents halogen, especially chlorine or bromine, corresponding to the halogen compound used for the 2,2'-anhydride formation. Acid addition salts with other physiologically acceptable acids can readily be obtained from the resulting hydrohalides if desired by ion-exchange in a manner known per se.

The esters of formula I belong to a known class of compounds (see, for example, German Offenlegungsschrift No. 2,112,724 in which there is also described a process for their manufacture by reacting cytidines with α-acyloxy-acyl halides) and are, as is known, for example, from German Offenlegungsschrift No. 2,363,536, valuable intermediates for the production of acid addition salts (especially of hydrohalides) of 2,2'-anhydro-1β-D-arabinofuranosyl-5-fluorocytosine, which is a known compound having antileukaemic and antiviral activity and which can be produced according to a known process (see, for example, German Offenlegungsschrift No. 2,342,930) by internal anhydride formation from 5-fluorocytidine.

The present process makes it possible to convert 5-fluorocytidine practically in a one-pot process into 2,2'-anhydro-1β-D-arabinofuranosyl-5-fluorocytosine.

The following Example illustrates the present invention:

EXAMPLE 24 g of p-toluenesulphonic acid are added while stirring and cooling with an ice-bath to a suspension of 24 g of 5-fluorocytidine in 60 ml of orthoacetic acid trimethyl ester. After a short time there is obtained a clear solution which is stirred at room temperature for 3 hours and then evaporated to dryness. To a solution of the resulting residue [2',3'-O,O-(1-methoxyethylidene)-5-fluorocytidine] in 150 ml of acetonitrile are then added dropwise under reflux and while stirring 30 ml of trimethylchlorosilane. After completion of the addition, the mixture is boiled under reflux for 10 minutes and then cooled to room temperature. To this mixture are added dropwise while stirring 400 ml of acetone and the resulting mixture is left to stand at room temperature overnight. There are obtained 27 g (90% of theory) of crystalline 3'-O-acetyl-2,2'-anhydro-1β-D-arabinofuranosyl-5-fluorocytosine hydrochloride. This hydrochloride is filtered off under suction, washed with 50 ml of acetone and 50 ml of ether and boiled under reflux for 20 minutes in 90 ml of 3 N hydrochloric acid. There is initially obtained a solution from which crystals separate out after a few minutes. The mixture is cooled to room temperature and, while stirring and cooling with an ice-bath, treated dropwise with 200 ml of isopropanol. After 3 hours, the crystalline 2,2'-anhydro-1β-D-arabinofuranosyl-5-fluorocytosine hydrochloride is filtered off under suction, washed with 50 ml of isopropanol and 50 ml of ether and dried at 60° C. in vacuo. The yield amounts to 18.0 g (71% of theory based on 5-fluorocytidine). The product melts at a temperature above 250° C.

We claim:

1. A mixed orthoester of the formula

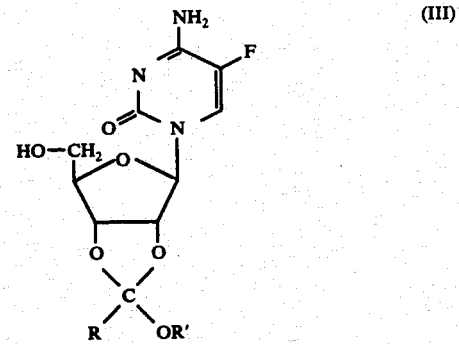

(III)

wherein R is alkyl containing from 1 to 6 carbon atoms and $R^1$ is alkyl containing from 1 to 3 carbon atoms.

2. The compound of claim 1 which is 2',3'-O,O-(1-methoxyethylidene)-5-fluorocytidine.